(12) United States Patent
Huelsen et al.

(10) Patent No.: US 8,913,133 B2
(45) Date of Patent: Dec. 16, 2014

(54) CAMERA SYSTEM FOR A MOTOR VEHICLE, AND MOTOR VEHICLE EQUIPPED WITH A CAMERA SYSTEM

(75) Inventors: Michael Huelsen, Stuttgart (DE); Ulrich Seger, Leonberg-Warmbronn (DE); Matthias Karl, Ettlingen (DE); Annette Frederiksen, Renningen (DE)

(73) Assignee: Robert Bosch GmbH, Stuttgart (DE)

( * ) Notice: Subject to any disclaimer, the term of this patent is extended or adjusted under 35 U.S.C. 154(b) by 753 days.

(21) Appl. No.: 13/138,022

(22) PCT Filed: Nov. 3, 2009

(86) PCT No.: PCT/EP2009/064523
§ 371 (c)(1),
(2), (4) Date: Oct. 21, 2011

(87) PCT Pub. No.: WO2010/076065
PCT Pub. Date: Jul. 8, 2010

(65) Prior Publication Data
US 2012/0026330 A1 Feb. 2, 2012

(30) Foreign Application Priority Data
Jan. 2, 2009 (DE) .......................... 10 2009 000 004

(51) Int. Cl.
| | | |
|---|---|---|
| *H04N 5/00* | (2011.01) | |
| *B60R 1/00* | (2006.01) | |
| *B60R 11/04* | (2006.01) | |
| *G01N 21/47* | (2006.01) | |
| *B60R 11/00* | (2006.01) | |
| *B60S 1/08* | (2006.01) | |
| *G01N 21/43* | (2006.01) | |

(52) U.S. Cl.
CPC . *B60R 1/00* (2013.01); *B60R 11/04* (2013.01); *G01N 21/47* (2013.01); *B60R 2011/0026* (2013.01); *B60R 2300/108* (2013.01); *B60R 2300/804* (2013.01); *B60S 1/0844* (2013.01); *G01N 2021/435* (2013.01); *G01N 2021/4709* (2013.01)
USPC .......................................................... 348/148

(58) Field of Classification Search
CPC ...................................................... H04N 5/225
USPC .......................................................... 348/148
See application file for complete search history.

(56) References Cited

U.S. PATENT DOCUMENTS

2007/0047948 A1* 3/2007 Tanida ......................... 396/332

FOREIGN PATENT DOCUMENTS

| DE | 103 23 560 | 12/2004 |
|---|---|---|
| DE | 10 2004 053 416 | 5/2006 |
| DE | 10 2005 000 650 | 7/2006 |

(Continued)

*Primary Examiner* — Sath V Perungavoor
*Assistant Examiner* — Jeffrey Williams
(74) *Attorney, Agent, or Firm* — Kenyon & Kenyon LLP

(57) ABSTRACT

A camera system for a motor vehicle includes: a camera, which includes an image sensor for outputting image signals, and camera optics for detecting a first environment and for imaging the first environment on the image sensor at a first subject distance. The camera system has camera supplementary optics, which are at least partially provided in the optical path in front of the camera optics, the camera optics and the camera supplementary optics jointly forming an optics system by which a second environment, e.g., a region of a surface of a window, is able to be imaged or focused on the image sensor at a second object distance that differs from the first object distance.

10 Claims, 2 Drawing Sheets

(56) References Cited

FOREIGN PATENT DOCUMENTS

| EP | 1 580 092 | 9/2005 | | |
| EP | 1580092 A2 * | 9/2005 | ............ | G03B 15/05 |
| EP | 2 062 777 | 5/2009 | | |
| WO | WO 2006/015905 | 2/2006 | | |

* cited by examiner

CAMERA SYSTEM FOR A MOTOR VEHICLE, AND MOTOR VEHICLE EQUIPPED WITH A CAMERA SYSTEM

BACKGROUND OF THE INVENTION

1. Field of the Invention

The present invention relates to a camera system for detecting an environment of a motor vehicle.

2. Description of Related Art

Camera systems for motor vehicles are generally known. For example, there are camera systems which are used for detecting an environment of a motor vehicle within the framework of a driver-assistance system. The image data of the vehicle environment recorded with the aid of the camera system can be used to aid a driver, e.g., in the form of a night-vision aid, for detecting traffic signs or road lane markings, or for monitoring traffic. In addition, it is known to use camera systems for detecting the state of a vehicle window.

Published German patent application document DE 103 23 560 A1 discloses a camera system for a motor vehicle, which is disposed in the interior of a vehicle, on a vehicle window, and records a region in front of the vehicle or a vehicle environment with the aid of a lens. With the help of a reflecting mirror, light incident approximately vertically above the motor vehicle is deflectable to the lens and thus able to be recorded by the image sensor. This light detected by the image sensor is evaluated in order to determine a brightness of the environment. The advantage of this system is that no additional light sensor is required for determining the brightness of the environment.

Published German patent application document DE 10 2005 000 650 A1 discloses another camera system for a motor vehicle for detecting an environment of a motor vehicle. The camera has an image sensor and camera optics which images the vehicle environment in clear detail on the image sensor. The camera system is disposed in a vehicle interior, on a vehicle window. Furthermore, the camera system includes a light source, in this case, an LED, with whose aid a subregion of the window is able to be illuminated. The image sensor is shielded from the light source by a reflecting mirror, in such a way that a portion of the illuminated window is able to be detected through a small subregion of the image sensor, the rest of the region of the image sensor being used for detecting the vehicle environment. The segment of the window that is able to be illuminated by the light source and detectable by the image sensor can be analyzed in order to determine wetting of the window by rain drops within the framework of a rain sensor function.

BRIEF SUMMARY OF THE INVENTION

The camera system for a motor vehicle according to the present invention is equipped with a camera which includes an image sensor and camera optics or a lens, through which an environment is detected in the usual manner, through a vehicle window, for example, and imaged or focused on the image sensor. In addition, according to the present invention a supplementary camera optical system is provided inside the optical path in front of the camera optics system, an additional environment being able to be focused on the image sensor with the aid of the entire camera optics system, which is made up of the camera optics and the additional camera optics system. In contrast to published German patent application document DE 103 23 560 A1, the object distance of the optics system made up of the camera optics and the supplementary camera optics for imaging on the image sensor differs from the subject distance of the camera optics. In particular, the camera optics may be focused on the infinite subject distance, and the optics system made up of camera optics and the supplementary camera optics may be focused on a finite value.

The camera system according to the present invention makes it possible to record different environments as separate, sharply focused images using only one image sensor. The first environment is the surroundings of a vehicle environment, in particular; the second environment may be an additional environment of the vehicle, e.g., an upward orientation for detecting informational traffic signs, or a lateral orientation in order to detect the road edges or in order to detect traffic signs, but especially also a vehicle window. The camera optics and the supplementary camera optics may have a static design, that is to say, be immovable. A complex system of movable optical elements such as lenses, with the goal of allowing different subject distances to be adjusted, is not absolutely necessary because the camera optics and the supplementary camera optics are provided.

In an advantageous manner, the image sensor has a first sensor range for detecting the first environment, and a second sensor range, which differs from the first range, for detecting the second environment. The second sensor range may, in particular, be formed laterally on the outside on the image sensor.

The camera according to the present invention thus simultaneously allows the evaluation of the imaging of the vehicle environment for functions such as lane detection, traffic sign detection or pedestrian detection, and the evaluation of the image of the vehicle window, in order to determine within the framework of a rain sensor function, for example, the wetting of the vehicle window by water droplets, or to detect soiling or damage of the window on the basis of sharply focused imaged details of a surface of the vehicle window. If appropriate, illumination of the vehicle window may be provided in addition, which allows an improved detection of wetting of the window by water droplets, soiling or damage of the window, with the aid of the camera.

The camera supplementary optics may be disposed fully in or on a camera holder for mounting the camera, in particular for affixation on a vehicle window. Thus, the camera holder with the entire camera supplementary optics and the camera may be implemented as separately exchangeable modules. As an alternative, the camera supplementary optics may also be mounted on the camera.

DETAILED DESCRIPTION OF THE INVENTION

Figure 1:
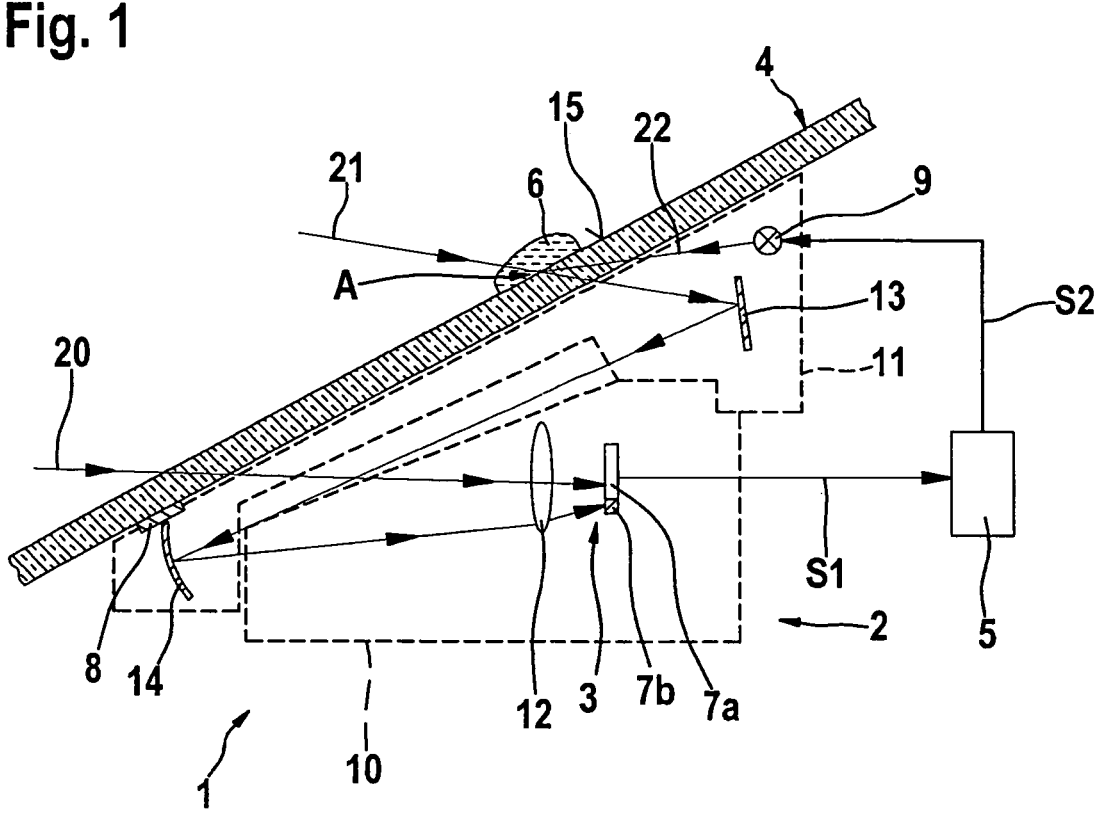
FIG. 1 shows a specific embodiment of a camera system according to the present invention.
Figure 2:
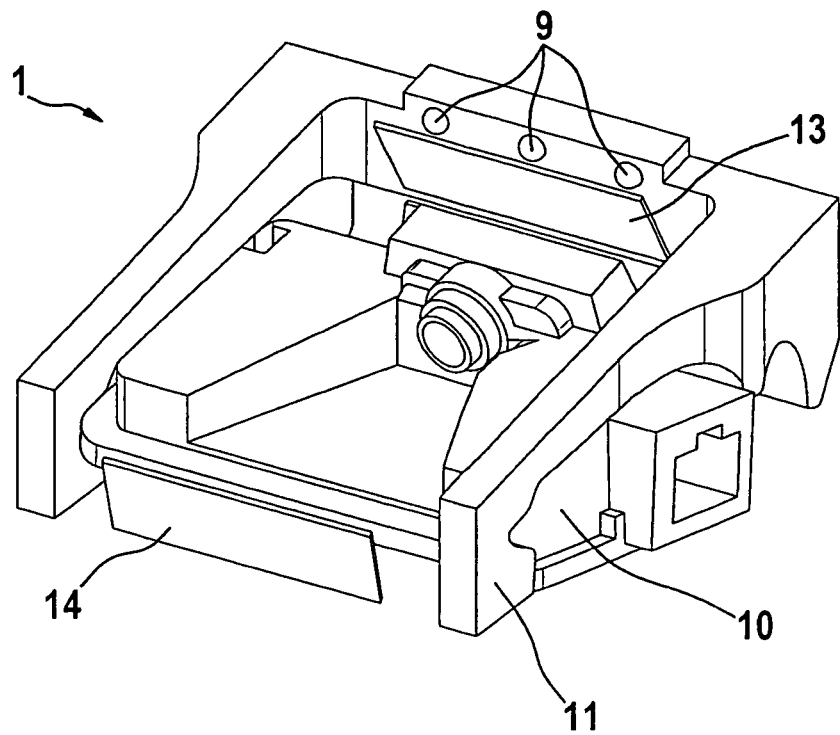
FIG. 2 shows a perspective view of the camera system.
Figure 3:
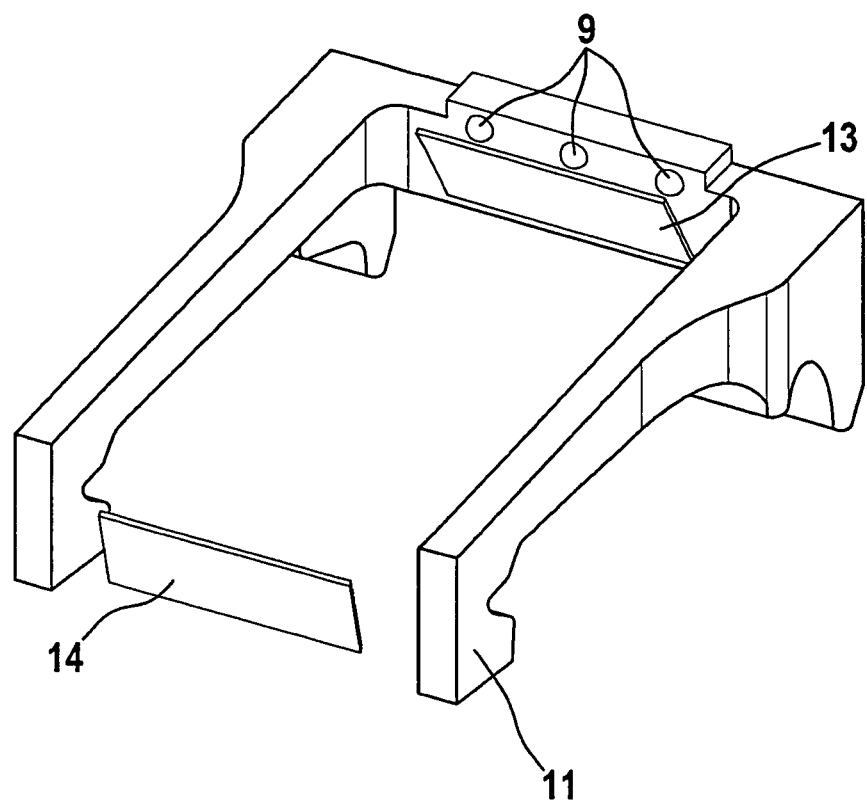
FIG. 3 shows a perspective view of a camera mount of the camera system.

Identical components or equivalent components in the figures have been provided with the same reference numerals.

A camera system 1 is designed for a motor vehicle for the purpose of detecting an environment. Camera system 1 includes a camera 2 and a camera mount 11. Camera mount 11 is fixed in place on a vehicle window 4, in this case, a windshield, in a vehicle interior of a motor vehicle (not shown further) and supports and positions camera 2. Camera 2 has a camera housing 10, an image sensor 3, as well as camera optics 12 (or lens), which is illustrated by a lens in this instance. Image sensor 3 is developed on a semiconductor basis, for example as CMOS or CCD component, which outputs image signals S1. A first environment, in this case, an environment of the vehicle that lies in front of the vehicle in the driving direction, for instance, is imaged by camera optics 12 through window 4 in sharply defined manner. Toward this end, first radiation 20 incident through vehicle window 4 is imaged or focused on a first sensor region 7a of image sensor 3.

According to the present invention, camera supplementary optics are provided in addition, which are implemented by a reflecting mirror 13 and a concave mirror 14 in this instance; alternatively or additionally, other optical elements such as lenses and/or optical diffraction gratings may be used as well. Camera supplementary optics 13, 14 is at least partially disposed in the optical path in front of camera optics 12, since concave mirror 14 lies within the detection range of camera optics 12. The optics system formed by camera supplementary optics 13, 14 and camera optics 12, images a sharply focused second environment, in this case, a section A of a window surface 15 of window 4, on image sensor 3. Thus, second radiation 21, emanating from segment A of vehicle window 4, or second radiation 21 passing through segment A, successively passes through camera supplementary optics 13, 14 and camera optics 12, and is imaged to or focused on a second sensor region 7b of image sensor 3 that differs from first sensor region 7a. Second radiation 21 may come from the environment of the vehicle, as sketched, and penetrate vehicle window 4, possibly also through a water droplet 6 adhering to it, or else it may also come from the interior of the vehicle and be reflected accordingly. In FIG. 1 the precise beam path through vehicle window 4 and water droplet 6 is not illustrated but simplified instead, for reasons of simplification and clarity.

In this exemplary embodiment, the subject distance or object distance of camera optics 12 is infinite, the subject distance or object distance of the shared optics system made up of camera optics 12 and camera supplementary optics 13, 14 is finite, and its focus lies in the region of vehicle window 4. Nevertheless, via a suitable distance between mirrors 13, 14, an object distance that is sufficiently large for imaging a region A, which is situated in relatively close proximity to camera 2, may be formed on image sensor 3 with excellent imaging properties. As an alternative, it is also possible to use optics 12, 13, 14 featuring different object distances.

In order to reduce the influencing of image sensor regions 7a, 7b by the radiation from segment A of window 4 or from the area of the vehicle environment, a diaphragm 8 is disposed in front of lens 12 in order to separate the two differently focused image data, so that a transition region in which the image information is blacked out is formed on image sensor 3 between first sensor region 7a and second sensor region 7b. As an alternative, such a diaphragm 3 may basically also be dispensed with.

Furthermore, camera system 1 includes an evaluation device 5, which is configured in such a way that it evaluates image signals S1, which include image data of first sensor region 7a and second sensor region 7b of image sensor 3. The image data of second environment A are evaluated here in order to determine a window state of vehicle window 4. In this case, evaluation device 5 is designed such that different wetting of segment A of vehicle window 4 by water droplets 6 is determined, in particular, so that this information may then be used within the framework of a rain sensor function, for example, such as for the control of a windshield wiper. As an alternative or in addition, it is also possible to determine soiling or damage of window 4 in this manner, for instance by scratches.

In addition, camera system 1 advantageously includes a light source 9, such as one or more LEDs, with whose aid segment A of vehicle window 4 is additionally able to be illuminated by radiation 22. For example, light source 9 is disposed such that radiation 22 reflected in the area of segment A is able to impinge upon image sensor 3 via camera supplementary optics 13, 14. Light source 9 makes it possible to illuminate segment A, especially when the light conditions are poor such as at night, so that an image of segment A that has sufficient brightness is produced on image sensor 3, the latter being advantageous for evaluating the window condition. Light source 9, as shown, may be controlled with the aid of control signals S2 from evaluation unit 5, which thus also constitutes a control unit, or else it may be controlled by some other device.

Thus, image sensor 3 and camera optics (lens) 12 are situated inside camera housing 10 of camera 2. Camera supplementary optics 13, 14, diaphragm 8, and light source 9 are disposed in or on camera mount 11, which consequently forms a separate module for this supplementary function of the window detection. However, as an alternative, it is also possible to provide at least parts of camera supplementary optics 13, 14, and/or diaphragm 8, and/or light source 9 on camera housing 10.

Evaluation unit 5 is advantageously situated inside camera housing 10, but may also be placed on the outside, for instance as a component of a central control unit of a vehicle assistance system.

Instead of being a segment A of vehicle window 4, the second environment may alternatively be an environment of the vehicle, for example, that detects a road edge, traffic signs situated along the road edge, or informational traffic signs situated above the vehicle, or else it may detect the vehicle interior, for which a subject distance that differs from that for the first environment is able to be adjusted in each case according to the present invention. The line of sight may be diverted via optical elements, especially mirrors.

What is claimed is:

1. A camera system for a motor vehicle, comprising:
   a camera having an image sensor for the output of image signals;
   camera optics for detecting a first environment and for imaging the first environment on the image sensor at a first subject lens distance; and
   camera supplementary optics at least partially provided in the optical path in front of the camera optics, the camera optics and the camera supplementary optics jointly forming an optics system by which a second environment is able to be imaged on the image sensor at a second object distance different from the first object distance, wherein the camera supplementary optics are disposed in or on a camera mount configured for fixation of the camera, and wherein the camera mount and the camera are separately exchangeable modules.

2. The camera system as recited in claim 1, wherein the first environment is a first vehicle environment recorded by the camera through a vehicle window, and the second environment is one of another vehicle environment or a region of a vehicle window.

3. The camera system as recited in claim 2, further comprising:
   an evaluation device configured to (i) record the image signals emitted by the image sensor and (ii) determine a window condition of the vehicle window on the basis of the image signals pertaining to the second environment, wherein the determining of the window condition includes at least determining wetting of the vehicle window by rain drops.

4. The camera system as recited claim 3, wherein the image sensor has a first sensor region for detecting the first environment, and a second sensor region different from the first sensor region, for detecting the second environment.

5. The camera system as recited in claim 4, wherein the camera additionally has a diaphragm for separating the first sensor region from the second sensor region.

6. The camera system as recited in claim 4, further comprising:
a light source for illuminating the second environment.

7. The camera system as recited in claim 4, wherein the camera supplementary optics have at least one mirror disposed inside the optical path of the camera optics.

8. The camera system as recited in claim 7, wherein the camera supplementary optics further include another optical element situated at a distance from the mirror, wherein at least one of the optical elements of the camera supplementary optics having a finite focal length.

9. The camera system as recited in claim 4, wherein the camera optics and the camera supplementary optics have a static design.

10. The camera system as recited in claim 4, wherein the camera system is disposed in a vehicle interior behind the vehicle window.

\* \* \* \* \*